(12) United States Patent
Divino

(10) Patent No.: US 10,828,037 B2
(45) Date of Patent: Nov. 10, 2020

(54) ELECTROLYTIC DETACHMENT WITH FLUID ELECTRICAL CONNECTION

(71) Applicant: Covidien LP, Mansfield, MA (US)

(72) Inventor: Vincent Divino, Mission Viejo, CA (US)

(73) Assignee: COVIDIEN LP, Mansfield, MA (US)

( * ) Notice: Subject to any disclaimer, the term of this patent is extended or adjusted under 35 U.S.C. 154(b) by 66 days.

(21) Appl. No.: 15/619,774

(22) Filed: Jun. 12, 2017

(65) Prior Publication Data

US 2017/0367707 A1 Dec. 28, 2017

Related U.S. Application Data

(60) Provisional application No. 62/354,939, filed on Jun. 27, 2016.

(51) Int. Cl.
| | | |
|---|---|---|
| *A61B 17/12* | (2006.01) | |
| *A61M 5/142* | (2006.01) | |
| *A61F 2/966* | (2013.01) | |
| *A61B 17/00* | (2006.01) | |
| *A61B 90/00* | (2016.01) | |

(52) U.S. Cl.
CPC .. *A61B 17/12109* (2013.01); *A61B 17/12031* (2013.01); *A61B 17/12113* (2013.01); *A61B 17/12145* (2013.01); *A61B 17/12172* (2013.01); *A61F 2/966* (2013.01); *A61M 5/142* (2013.01); *A61B 2017/00017* (2013.01); *A61B 2017/00867* (2013.01); *A61B 2017/00929* (2013.01); *A61B 2017/12063* (2013.01); *A61B 2090/3966* (2016.02); *A61B 2217/007* (2013.01)

(58) Field of Classification Search
CPC .. A61B 2017/12063; A61B 2017/1205–12095
See application file for complete search history.

(56) References Cited

U.S. PATENT DOCUMENTS

| | | |
|---|---|---|
| 5,108,407 A | 4/1992 | Geremia et al. |
| 5,122,136 A | 6/1992 | Guglielmi et al. |
| 5,250,071 A | 10/1993 | Palermo |
| 5,354,295 A | 10/1994 | Guglielmi et al. |

(Continued)

FOREIGN PATENT DOCUMENTS

| | | |
|---|---|---|
| DE | 4445715 A1 | 6/1996 |
| EP | 1884208 A1 | 2/2008 |

(Continued)

*Primary Examiner* — Katrina M Stransky
*Assistant Examiner* — Brigid K Byrd
(74) *Attorney, Agent, or Firm* — Fortem IP LLP; Matthew Lincicum

(57) ABSTRACT

Detachment of an implant from a delivery assembly can be electrolytic and provide an electrical current pathway through a fluid within a portion of a delivery system containing the delivery assembly. After the implant is located at a target location within a patient, a voltage potential is applied between (i) a delivery electrode electrically connected to an electrolytic detachment zone and (ii) an infusion electrode disposed outside of the patient and electrically connected to the electrolytic detachment zone via a fluid from a fluid source disposed outside of the patient. While applying the voltage potential, the fluid can be flushed from the fluid source past the detachment zone.

16 Claims, 8 Drawing Sheets

(56) References Cited

U.S. PATENT DOCUMENTS

| | | | |
|---|---|---|---|
| 5,370,653 A | 12/1994 | Cragg | |
| 5,423,829 A | 6/1995 | Pham et al. | |
| 5,509,411 A | 4/1996 | Littmann et al. | |
| 5,522,836 A | 6/1996 | Palermo | |
| 5,540,680 A | 7/1996 | Guqlielmi et al. | |
| 5,624,449 A | 4/1997 | Pham et al. | |
| 5,658,308 A | 8/1997 | Snyder | |
| 5,669,931 A | 9/1997 | Kupiecki et al. | |
| 5,690,667 A | 11/1997 | Gia | |
| 5,733,329 A | 3/1998 | Wallace et al. | |
| 5,743,905 A | 4/1998 | Eder et al. | |
| 5,749,894 A | 5/1998 | Engelson | |
| 5,766,629 A | 6/1998 | Cho et al. | |
| 5,800,455 A | 9/1998 | Palermo et al. | |
| 5,851,206 A | 12/1998 | Guglielmi et al. | |
| 5,853,418 A | 12/1998 | Ken et al. | |
| 5,855,578 A | 1/1999 | Guglielmi et al. | |
| 5,891,128 A | 4/1999 | Gia et al. | |
| 5,895,385 A | 4/1999 | Guqlielmi et al. | |
| 5,916,235 A | 6/1999 | Guglielmi | |
| 5,919,187 A | 7/1999 | Guqlielmi et al. | |
| 5,925,037 A | 7/1999 | Guglielmi et al. | |
| 5,925,059 A | 7/1999 | Palermo et al. | |
| 5,928,226 A | 7/1999 | Guqlielmi et al. | |
| 5,935,145 A | 8/1999 | Villar et al. | |
| 5,941,888 A | 8/1999 | Wallace et al. | |
| 5,944,114 A | 8/1999 | Guglielmi et al. | |
| 5,947,962 A | 9/1999 | Guglielmi et al. | |
| 5,947,963 A | 9/1999 | Guqlielmi | |
| 5,951,599 A | 9/1999 | McCrory | |
| 5,964,797 A | 10/1999 | Ho | |
| 5,976,126 A | 11/1999 | Guglielmi | |
| 5,984,929 A | 11/1999 | Bashiri et al. | |
| 6,010,498 A | 1/2000 | Guqlielmi | |
| 6,013,084 A | 1/2000 | Ken et al. | |
| 6,059,779 A * | 5/2000 | Mills | A61B 17/12022 600/373 |
| 6,063,070 A | 5/2000 | Eder | |
| 6,063,104 A | 5/2000 | Villar et al. | |
| 6,066,133 A | 5/2000 | Guglielmi et al. | |
| 6,077,260 A | 6/2000 | Wheelock et al. | |
| 6,083,220 A | 7/2000 | Guglielmi et al. | |
| 6,123,714 A | 9/2000 | Gia et al. | |
| 6,136,015 A | 10/2000 | Kurz et al. | |
| 6,146,373 A | 11/2000 | Cragg et al. | |
| 6,156,061 A | 12/2000 | Wallace et al. | |
| 6,165,178 A | 12/2000 | Bashiri et al. | |
| 6,168,592 B1 | 1/2001 | Kupiecki et al. | |
| 6,168,615 B1 | 1/2001 | Ken et al. | |
| 6,168,618 B1 | 1/2001 | Frantzen | |
| 6,193,728 B1 | 2/2001 | Ken et al. | |
| 6,238,403 B1 | 5/2001 | Greene, Jr. et al. | |
| 6,241,691 B1 | 6/2001 | Ferrera et al. | |
| 6,280,457 B1 | 8/2001 | Wallace et al. | |
| 6,296,622 B1 | 10/2001 | Kurz et al. | |
| 6,299,619 B1 | 10/2001 | Greene, Jr. et al. | |
| 6,306,153 B1 | 10/2001 | Kurz et al. | |
| 6,309,367 B1 | 10/2001 | Boock | |
| 6,371,972 B1 | 4/2002 | Wallace et al. | |
| 6,409,721 B1 | 6/2002 | Wheelock et al. | |
| 6,416,373 B1 | 7/2002 | Kolb et al. | |
| 6,425,893 B1 * | 7/2002 | Guglielmi | A61B 17/12022 606/108 |
| 6,425,914 B1 | 7/2002 | Wallace et al. | |
| 6,468,266 B1 | 10/2002 | Bashiri et al. | |
| 6,468,301 B1 | 10/2002 | Amplatz et al. | |
| 6,478,773 B1 | 11/2002 | Gandhi et al. | |
| 6,485,524 B2 | 11/2002 | Strecker | |
| 6,486,266 B2 | 11/2002 | Amano et al. | |
| 6,511,468 B1 | 1/2003 | Craaa et al. | |
| 6,533,801 B2 | 3/2003 | Wallace et al. | |
| 6,558,367 B1 | 5/2003 | Craaa et al. | |
| 6,589,230 B2 | 7/2003 | Gia et al. | |
| 6,589,236 B2 | 7/2003 | Wheelock et al. | |
| 6,602,261 B2 | 8/2003 | Greene, Jr. et al. | |
| 6,605,101 B1 | 8/2003 | Schaefer et al. | |
| 6,620,152 B2 | 9/2003 | Guqlielmi | |
| 6,623,493 B2 | 9/2003 | Wallace et al. | |
| 6,723,112 B2 | 4/2004 | Ho et al. | |
| 6,743,251 B1 | 6/2004 | Eder | |
| 6,835,185 B2 | 12/2004 | Ramzipoor et al. | |
| 6,878,384 B2 | 4/2005 | Cruise et al. | |
| 6,905,503 B2 | 6/2005 | Gifford, III et al. | |
| 6,936,055 B1 | 8/2005 | Ken et al. | |
| 6,953,473 B2 | 10/2005 | Porter | |
| 6,964,657 B2 | 11/2005 | Craaa et al. | |
| 6,966,892 B2 | 11/2005 | Gandhi et al. | |
| 7,014,645 B2 | 3/2006 | Greene, Jr. et al. | |
| 7,083,567 B2 | 8/2006 | Mawad | |
| 7,128,736 B1 | 10/2006 | Abrams et al. | |
| 7,166,122 B2 | 1/2007 | Aqanon et al. | |
| 7,169,172 B2 | 1/2007 | Levine et al. | |
| 7,198,613 B2 | 4/2007 | Gandhi et al. | |
| 7,229,461 B2 | 6/2007 | Chin et al. | |
| 7,238,194 B2 | 7/2007 | Monstadt et al. | |
| 7,255,707 B2 | 8/2007 | Ramzipoor et al. | |
| 7,300,458 B2 | 11/2007 | Henkes et al. | |
| 7,323,000 B2 | 1/2008 | Monstdt et al. | |
| 7,331,974 B2 | 2/2008 | Schaefer et al. | |
| 7,485,122 B2 | 2/2009 | Teoh | |
| 7,524,322 B2 | 4/2009 | Monstdt et al. | |
| 7,601,160 B2 | 10/2009 | Richter | |
| 7,608,089 B2 | 10/2009 | Wallace et al. | |
| RE41,029 E | 12/2009 | Guglielmi et al. | |
| 7,651,513 B2 | 1/2010 | Teoh et al. | |
| 7,695,484 B2 | 4/2010 | Wallace et al. | |
| 7,879,064 B2 | 2/2011 | Monstadt et al. | |
| 7,896,899 B2 | 3/2011 | Patterson et al. | |
| 7,938,845 B2 | 5/2011 | Aganon et al. | |
| RE42,625 E | 8/2011 | Guglielmi | |
| 8,002,789 B2 | 8/2011 | Ramzipoor et al. | |
| RE42,756 E | 9/2011 | Guqlielmi et al. | |
| 8,016,869 B2 | 9/2011 | Nikolchev | |
| 8,021,416 B2 | 9/2011 | Abrams | |
| 8,043,326 B2 | 10/2011 | Hancock et al. | |
| 8,048,104 B2 | 11/2011 | Monstadt et al. | |
| RE43,311 E | 4/2012 | Wallace et al. | |
| 8,157,855 B2 | 4/2012 | Eidenschink et al. | |
| 8,202,292 B2 | 6/2012 | Kellett | |
| 8,221,396 B2 | 7/2012 | Dehnad et al. | |
| 8,221,483 B2 | 7/2012 | Ford et al. | |
| 8,273,116 B2 | 9/2012 | Licata et al. | |
| 8,298,256 B2 | 10/2012 | Gandhi et al. | |
| 8,328,860 B2 | 12/2012 | Strauss et al. | |
| 8,372,110 B2 | 2/2013 | Monstadt et al. | |
| 8,398,671 B2 | 3/2013 | Chen et al. | |
| 8,425,541 B2 | 4/2013 | Masters et al. | |
| 8,470,013 B2 | 6/2013 | Duggal et al. | |
| 8,480,701 B2 | 7/2013 | Monstadt | |
| 8,562,667 B2 | 10/2013 | Cox | |
| 8,597,321 B2 | 12/2013 | Monstadt et al. | |
| 8,632,584 B2 | 1/2014 | Henkes et al. | |
| 8,641,746 B2 | 2/2014 | Andreas et al. | |
| 8,641,777 B2 | 2/2014 | Strauss et al. | |
| 8,652,163 B2 | 2/2014 | Padilla et al. | |
| 8,657,870 B2 | 2/2014 | Turovskiv et al. | |
| 8,715,312 B2 | 5/2014 | Burke et al. | |
| 8,715,317 B1 | 5/2014 | Janardhan et al. | |
| 8,721,625 B2 | 5/2014 | Klint | |
| 8,728,142 B2 | 5/2014 | Gandhi et al. | |
| 8,777,978 B2 | 7/2014 | Strauss et al. | |
| 8,777,979 B2 | 7/2014 | Shrivastava et al. | |
| 8,795,320 B2 | 8/2014 | Strauss et al. | |
| 8,795,321 B2 | 8/2014 | Strauss et al. | |
| 8,801,747 B2 | 8/2014 | Strauss et al. | |
| 8,845,676 B2 | 9/2014 | Monstadt et al. | |
| 8,864,790 B2 | 10/2014 | Strauss et al. | |
| 8,870,909 B2 | 10/2014 | Cox | |
| 8,876,863 B2 | 11/2014 | Eskridge | |
| 8,900,285 B2 | 12/2014 | Licata | |
| 8,906,057 B2 | 12/2014 | Connor et al. | |
| 8,915,950 B2 | 12/2014 | Cam et al. | |
| 8,926,681 B2 | 1/2015 | Levv et al. | |
| 8,932,317 B2 | 1/2015 | Marks et al. | |

(56) References Cited

U.S. PATENT DOCUMENTS

| | | |
|---|---|---|
| 8,940,011 B2 | 1/2015 | Teoh et al. |
| 8,974,509 B2 | 3/2015 | Licata |
| 8,974,513 B2 | 3/2015 | Ford et al. |
| 8,992,563 B2 | 3/2015 | Chen |
| 8,998,926 B2 | 4/2015 | Pomeranz |
| 9,039,749 B2 | 5/2015 | Shrivastava et al. |
| 9,050,095 B2 | 6/2015 | Monstadt et al. |
| 9,055,948 B2 | 6/2015 | Jaeqer et al. |
| 9,211,202 B2 | 12/2015 | Strother et al. |
| 9,486,224 B2 | 11/2016 | Riina et al. |
| 9,833,309 B2 | 12/2017 | Levi et al. |
| 9,844,380 B2 | 12/2017 | Furey |
| 9,907,684 B2 | 3/2018 | Connor et al. |
| 9,962,146 B2 | 5/2018 | Hebert et al. |
| 10,028,745 B2 | 7/2018 | Morsi |
| 2001/0000797 A1 | 5/2001 | Mazzocchi |
| 2001/0001835 A1 | 5/2001 | Greene et al. |
| 2002/0151883 A1 | 10/2002 | Guqlielmi |
| 2003/0014073 A1 | 1/2003 | Bashiri et al. |
| 2003/0018294 A1 | 1/2003 | Cox |
| 2003/0028209 A1 | 2/2003 | Teoh et al. |
| 2003/0040733 A1 | 2/2003 | Craaa et al. |
| 2003/0040772 A1 | 2/2003 | Hyodoh et al. |
| 2003/0060833 A1 | 3/2003 | Carrison et al. |
| 2003/0176857 A1 | 9/2003 | Lee |
| 2003/0212426 A1 | 11/2003 | Olson |
| 2003/0225365 A1 | 12/2003 | Greff et al. |
| 2004/0002731 A1 | 1/2004 | Aqanon et al. |
| 2004/0225279 A1 | 11/2004 | Ravmond |
| 2004/0236344 A1 | 11/2004 | Monstadt et al. |
| 2005/0079196 A1 | 4/2005 | Henkes et al. |
| 2005/0267511 A1 | 12/2005 | Marks et al. |
| 2006/0036281 A1 | 2/2006 | Patterson et al. |
| 2006/0100602 A1 | 5/2006 | Klint |
| 2006/0135986 A1 | 6/2006 | Wallace et al. |
| 2006/0155323 A1 | 7/2006 | Porter et al. |
| 2006/0200234 A1 | 9/2006 | Hines |
| 2006/0206199 A1 | 9/2006 | Churchwell et al. |
| 2006/0271097 A1 | 11/2006 | Ramzipoor et al. |
| 2007/0073334 A1 | 3/2007 | Ramzipoor |
| 2007/0100426 A1 | 5/2007 | Rudakov et al. |
| 2007/0175536 A1 | 8/2007 | Monetti et al. |
| 2007/0191924 A1 | 8/2007 | Rudakov |
| 2008/0045922 A1 | 2/2008 | Craaa et al. |
| 2008/0051803 A1 | 2/2008 | Monjtadt et al. |
| 2008/0103585 A1 | 5/2008 | Monstadt et al. |
| 2008/0125855 A1 | 5/2008 | Henkes et al. |
| 2008/0221666 A1 | 9/2008 | Licata et al. |
| 2008/0228215 A1 | 9/2008 | Strauss et al. |
| 2008/0228216 A1 | 9/2008 | Strauss et al. |
| 2008/0319532 A1 | 12/2008 | Monstadt et al. |
| 2009/0062726 A1* | 3/2009 | Ford ............ A61B 17/12022 604/57 |
| 2009/0143786 A1 | 6/2009 | Bashiri et al. |
| 2009/0227976 A1 | 9/2009 | Calabria |
| 2009/0254111 A1 | 10/2009 | Monstadt et al. |
| 2010/0023105 A1 | 1/2010 | Levv et al. |
| 2010/0030200 A1 | 2/2010 | Strauss et al. |
| 2010/0049165 A1 | 2/2010 | Sutherland et al. |
| 2010/0063572 A1 | 3/2010 | Teoh et al. |
| 2010/0076479 A1 | 3/2010 | Monstadt |
| 2010/0094395 A1* | 4/2010 | Kellett ............ A61B 17/12022 623/1.11 |
| 2010/0144895 A1 | 6/2010 | Porter |
| 2010/0256666 A1 | 10/2010 | Chen et al. |
| 2010/0268204 A1 | 10/2010 | Tieu et al. |
| 2010/0331948 A1 | 12/2010 | Turovskiy et al. |
| 2011/0098814 A1 | 4/2011 | Monstadt et al. |
| 2011/0106128 A1 | 5/2011 | Chen |
| 2011/0118768 A1 | 5/2011 | Tran et al. |
| 2011/0118777 A1 | 5/2011 | Patterson et al. |
| 2011/0137405 A1 | 6/2011 | Wilson et al. |
| 2011/0184453 A1 | 7/2011 | Levy et al. |
| 2012/0010648 A1 | 1/2012 | Monstadt et al. |
| 2012/0209310 A1 | 8/2012 | Chen et al. |
| 2012/0271344 A1 | 10/2012 | Ford et al. |
| 2012/0316632 A1 | 12/2012 | Gao |
| 2013/0138198 A1 | 5/2013 | Aporta et al. |
| 2013/0184743 A1 | 7/2013 | Chen et al. |
| 2013/0211492 A1 | 8/2013 | Schneider et al. |
| 2013/0274866 A1 | 10/2013 | Cox et al. |
| 2013/0296917 A1* | 11/2013 | Rees ............... A61B 17/12022 606/200 |
| 2014/0005651 A1 | 1/2014 | Eskridqe |
| 2014/0012307 A1 | 1/2014 | Franano et al. |
| 2014/0039535 A1 | 2/2014 | Eskuri |
| 2014/0058420 A1 | 2/2014 | Hannes et al. |
| 2014/0135818 A1 | 5/2014 | Gandhi et al. |
| 2014/0142608 A1 | 5/2014 | Eskridge et al. |
| 2014/0148843 A1 | 5/2014 | Strauss et al. |
| 2014/0163604 A1 | 6/2014 | Monstadt |
| 2014/0236217 A1 | 8/2014 | Gandhi et al. |
| 2014/0277092 A1 | 9/2014 | Teoh et al. |
| 2014/0277094 A1 | 9/2014 | Chen et al. |
| 2014/0288633 A1 | 9/2014 | Burke et al. |
| 2014/0316012 A1 | 10/2014 | Freyman et al. |
| 2014/0371734 A1 | 12/2014 | Truckai |
| 2014/0371839 A1 | 12/2014 | Henkes et al. |
| 2015/0005804 A1 | 1/2015 | Franano et al. |
| 2015/0057700 A1 | 2/2015 | Chen et al. |
| 2015/0066073 A1 | 3/2015 | Ma |
| 2015/0105817 A1 | 4/2015 | Marchand et al. |
| 2015/0133990 A1 | 5/2015 | Davidson |
| 2015/0142042 A1 | 5/2015 | Cox |
| 2015/0150563 A1 | 6/2015 | Marchand et al. |
| 2015/0157331 A1 | 6/2015 | Levy et al. |
| 2015/0164665 A1 | 6/2015 | Cam et al. |
| 2015/0173771 A1 | 6/2015 | Marks et al. |
| 2015/0216684 A1 | 8/2015 | Enzmann et al. |
| 2015/0250628 A1 | 9/2015 | Monstadt et al. |
| 2015/0313737 A1 | 11/2015 | Tippett et al. |
| 2015/0327843 A1 | 11/2015 | Garrison |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0331377 A1* | 11/2016 | Divino ............ A61B 17/12022 |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |

FOREIGN PATENT DOCUMENTS

| | | |
|---|---|---|
| EP | 2668914 A1 | 12/2013 |
| WO | 2011066962 A1 | 6/2011 |
| WO | WO-2014078286 | 5/2014 |
| WO | 2017074411 A1 | 5/2017 |
| WO | 2018051187 A1 | 3/2018 |

* cited by examiner

ELECTROLYTIC DETACHMENT WITH FLUID ELECTRICAL CONNECTION

RELATED APPLICATIONS

This application claims priority to provisionally filed U.S. Patent Application No. 62/354,939 filed Jun. 27, 2016, which is incorporated herein by reference in its entirety.

TECHNICAL FIELD

The subject technology relates to the delivery of implantable medical devices and systems for delivering implantable medical devices.

BACKGROUND

The use of endovascular techniques for the implantation of medical devices for the treatment and the occlusion of body cavities such as arteries, veins, fallopian tubes or vascular deformities is known in the art. For example, vascular aneurysms can be occluded with an implantable medical device that is introduced to the vasculature with a delivery wire through a catheter. Once advanced to the treatment site, the medical device can be inserted into the aneurysm cavity to occlude the aneurysm and then detached from the delivery wire.

SUMMARY

Detachment of a medical device or implant from the delivery wire can be problematic. It is essential that the implant can be collapsed to form as small a profile as possible to be guided through the fine bore of the catheter, and it must bring about a reliable severance of the implant from the wire. Absent a reliable severance of the implant, withdrawal of the delivery wire and catheter may cause unintended removal of the implant from the aneurysm, and thus injure and/or rupture of the wall of the aneurysm or vessel.

While some mechanical methods for the detachment of implants are reliable, the rigidity of the connection between the implant and the delivery means necessary for such methods can impede the introduction of the implant. Furthermore, the low load carrying capacity of the connection (due to its rigidity) entails an appreciable risk of premature detachment of the insertion means from the occluding implant. Moreover, in the case of mechanical separation of the delivery wire and the implant, mechanical energy must be transmitted (e.g., by rotation of the delivery wire), which may cause the implant to be dislodged out of the correct position.

Electrolytic detachment of an implantable medical device can involve using an electrolytically corrodible region on the end of a delivery wire at the connection between the delivery wire and the medical device. Known methods of electrolytic detachment can employ an electrolytically corrodible region on the end of the delivery wire at the connection between the delivery wire and the implant. However, the connection of the implant to the delivery wire is limited by the requirements of the electrolytically corrodible region. For example, only materials that have a sufficiently high degree of strength to enable reliable guidance of the implant can be utilized in delivery wire material selection.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause (1 and 16). The other clauses can be presented in a similar manner.

1. A delivery system comprising:
   a catheter having a proximal end region, a distal end region, and a lumen extending from the proximal end region to the distal end region along a length that facilitates access from an entry region outside of a patient to a target location within the patient;
   a delivery wire extending through at least a portion of the lumen;
   an implant attached to the delivery wire by an electrolytically corrodible detachment zone;
   a fluid source disposed outside of the lumen and in fluid communication with the distal end region via the proximal end region and the lumen;
   a delivery electrode contacting the delivery wire and electrically connected to the electrolytically corrodible detachment zone via the delivery wire; and
   an infusion electrode contacting fluid within the lumen, the infusion electrode electrically connected to the electrolytically corrodible detachment zone via the fluid within the lumen.

2. The delivery system of example 1, further comprising a pump configured to provide a flow of the fluid within the lumen to the detachment zone.

3. The delivery system of example 1 or example 2, further comprising a power supply connected to the delivery electrode and the infusion electrode.

4. The delivery system of example 3, wherein the power supply is configured to provide a voltage potential between the delivery electrode and the infusion electrode.

5. The delivery system of any one of examples 1-4, wherein at least a portion of the outer surface of the delivery wire is electrically insulated.

6. The delivery system of any one of examples 1-5, wherein the delivery electrode contacts the delivery wire at the entry region outside the patient.

7. The delivery system of any one of examples 1-6, wherein the infusion electrode contacts the fluid at the entry region outside the patient.

8. The delivery system of any one of examples 1-7, further comprising an electrode interface connected to the proximal end region and configured to receive at least a portion of the infusion electrode to a space containing the fluid.

9. The delivery system of any one of examples 1-8, wherein the detachment zone is of a material that is more susceptible to electrolytic corrosion than a material of the delivery wire or a material of the implant.

10. The delivery system of any one of examples 1-9, wherein the fluid comprises saline.

11. The delivery system of any one of examples 1-10, wherein a distal tip of the infusion electrode is positioned within the lumen within 2 inches of the detachment zone.

12. The delivery system of any one of examples 1-11, wherein a distal tip of the infusion electrode is positioned within the lumen within 1 inch of the detachment zone.

13. The delivery system of any one of examples 1-10, wherein the infusion electrode extends within the sidewall from the proximal end region of the catheter to the distal end region of the catheter.

14. The delivery system of example 13, wherein a portion of the infusion electrode is exposed through the sidewall within 2 inches of the detachment zone.

15. The delivery system of example 13, wherein a portion of the infusion electrode is exposed through the sidewall within 1 inch of the detachment zone.

16. A method of delivering an implant, the method comprising:
   positioning the implant at a target location within a patient, the implant being attached to a delivery wire by an electrolytically corrodible detachment zone;
   applying a voltage potential between (i) a delivery electrode electrically connected to the electrolytically corrodible detachment zone via the delivery wire and (ii) an infusion electrode disposed outside of the patient and electrically connected to the electrolytically corrodible detachment zone via a fluid from a fluid source disposed outside of the patient; and
   while applying the voltage potential, flushing the fluid from the fluid source past the electrolytically corrodible detachment zone.

17. The method of example 16, wherein positioning the implant comprises:
   positioning a catheter with a proximal end region outside the patient and a distal end region at the target location; and
   advancing the implant through a lumen of the catheter.

18. The method of example 17, wherein applying the voltage potential comprises:
   connecting the delivery electrode to a portion of the delivery wire disposed outside of the patient; and
   connecting the infusion electrode to a portion of the catheter disposed outside of the patient.

19. The method of any one of examples 16-18, wherein applying the voltage potential comprises applying a voltage potential between the delivery electrode and the infusion electrode.

20. The method of any one of examples 16-19, wherein applying the voltage potential comprises:
   connecting the delivery electrode to a portion of the delivery wire disposed outside of the patient; and
   connecting the infusion electrode to a portion of the fluid source disposed outside of the patient.

21. The method of any one of examples 16-20, wherein applying the voltage potential comprises applying the voltage potential until the detachment zone has corroded.

22. The method of any one of examples 16-21, wherein the voltage potential is applied until the implant is separated from the delivery wire.

23. The method of any one of examples 16-22, wherein the fluid is flushed until the implant is separated from the delivery wire.

24. The method of any one of examples 16-23, wherein at least a portion of an outer surface of the delivery wire is electrically insulated.

25. The method of any one of example 16-24, wherein the fluid comprises saline.

26. The method of any one of examples 16-25, wherein positioning the implant at a target location is through a lumen of a catheter, and wherein a distal tip of the infusion electrode is positioned within the lumen within 2 inches of the detachment zone.

27. The method of any one of examples 16-26, wherein positioning the implant at a target location is through a lumen of a catheter, and wherein a distal tip of the infusion electrode is positioned within the lumen within 1 inch of the detachment zone.

28. The method of any one of examples 16-25, wherein the infusion electrode extends within the sidewall from the proximal end region of the catheter to the distal end region of the catheter.

29. The method of example 28, wherein a portion of the infusion electrode is exposed through the sidewall within 2 inches of the detachment zone.

30. The method of example 28, wherein a portion of the infusion electrode is exposed through the sidewall within 1 inch of the detachment zone.

It is to be understood that both the foregoing general description and the following detailed description are exemplifying and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

Implants can be implanted in body cavities, including blood vessels. Implants can be delivered to a target body cavity using a delivery system, and detached from the delivery system when positioned within the body cavity. A delivery system can comprise a delivery wire having an electrolytically corrodible detachment zone between the implant and the delivery system. When a voltage potential is applied across the detachment zone while in an electrolyte, such as blood for example, the detachment zone corrodes. When sufficiently corroded, the detachment zone is severed, releasing the implant from the delivery system.

In some delivery systems, the voltage potential can be generated using a power supply electrically connected to the delivery system. The power supply or ground can be electrically connected to a patient on the surface of the patient's skin to provide a conductive pathway from a detachment zone at or near the implant. The conductive pathway can require a secure connection, such as with a transcutaneous needle or other device that punctures the patient. The current would then flow through the patient and the needle between the detachment zone and the ground or power supply.

Whereas some systems require a needle puncturing the patient to complete a conductive pathway, an electrical connection to a detachment zone can be achieved without puncturing the patient. According to one or more aspects of the subject technology, electrolytic detachment can be facilitated by a closed circuit of electrical current entirely within a delivery system, thereby avoiding the need to insert a needle into the patient to complete a circuit through the patient's tissue. Thus, patient comfort is improved and resistance within the circuit is reduced, thereby improving detachment time and reliability.

Figure 1:
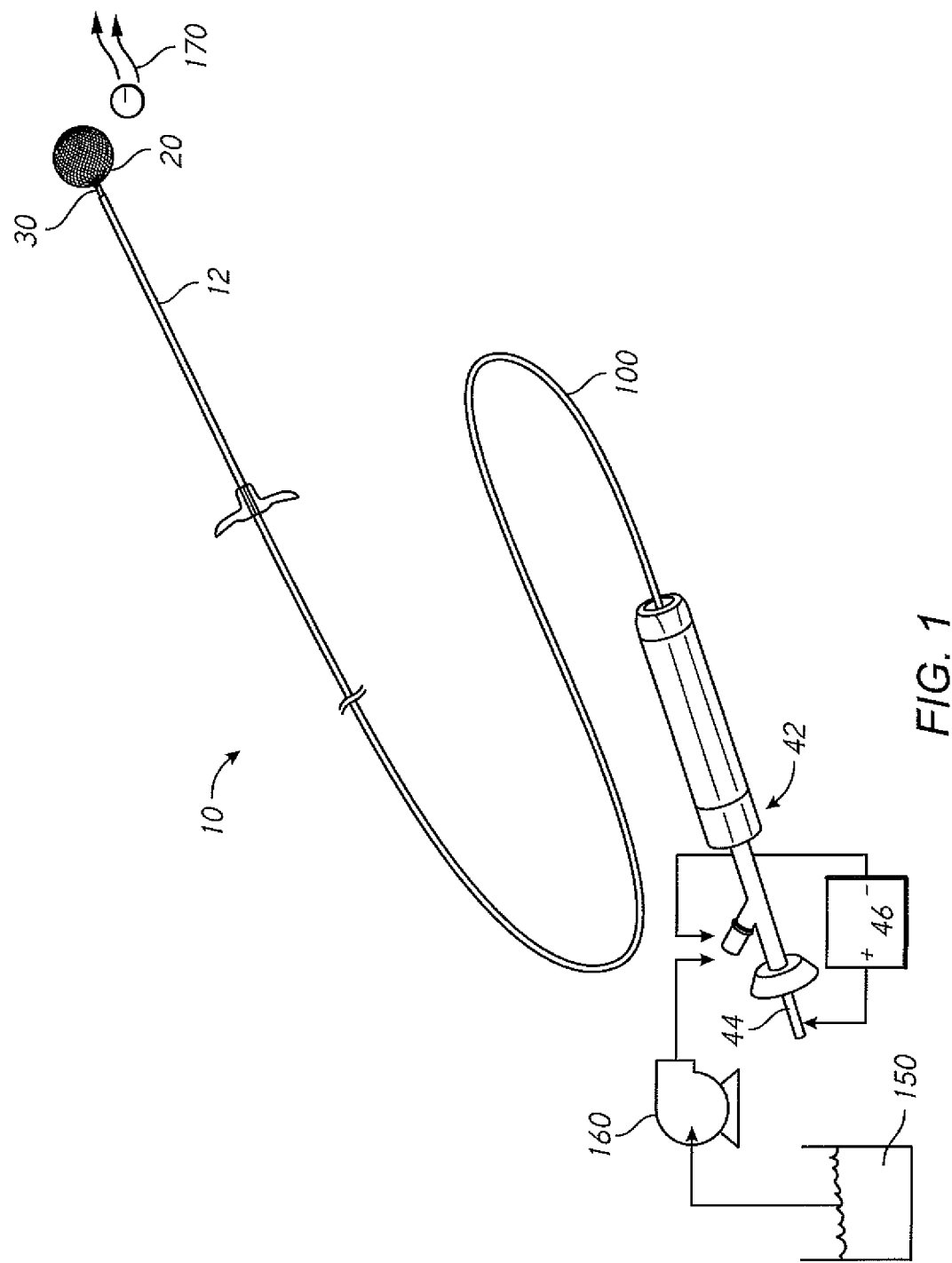
FIG. 1 shows a perspective view of a delivery system having an electrical return path, in accordance with one or more embodiments of the present disclosure.

FIG. 1 illustrates a view of a delivery system 10 according to one or more embodiments of the subject technology. According to some embodiments, for example, as shown in FIG. 1, the delivery system 10 can include an implant 20, a pusher assembly 12, and a delivery catheter 100 connected to a handle 42. The handle 42 shown provides proximal access to a delivery wire 44 of the pusher assembly 12 that engages the implant 20 at a distal end thereof. The delivery wire 44 can be connected to the implant at a detachment zone 30 forming a detachment junction between the delivery wire 44 and the implant 20 at or near the implant 20. The delivery catheter 100 can be positioned over the pusher assembly 12. According to some embodiments, the power supply 46 can be coupled to a proximal portion of the delivery wire 44, and the power supply 46 also can be coupled (e.g., to the handle 42) such that one of the terminals of the power supply 46 is in electrical connection with a fluid and/or fluid flow 170 in a vicinity of the implant 20, as described further herein.

According to some embodiments, the power supply 46 can include an electrical generator configured to output medically useful electrical current. The power supply 46 may be a direct current power supply, an alternating current power supply, or a power supply switchable between a direct current and an alternating current. The power supply 46 can include a suitable controller that can be used to control various parameters of the energy output by the generator, such as intensity, amplitude, duration, frequency, duty cycle, and polarity. For example, the power supply 46 can provide a voltage of about 12 volts to about 28 volts and a current of about 1 mA to about 2 mA.

According to some embodiments, for example as shown in FIG. 1, a fluid source 150 may be provided in fluid connection with a pump 160 for infusion of the fluid via the delivery catheter 100. The fluid source 150 can include saline or another sterile, electrolytic, biocompatible solution. The fluid can be infused together with a drug, such as heparin. The pump can draw fluid from the fluid source 150 and advance the fluid into and through a lumen 124 (FIG. 6) of the delivery catheter 100. The pump 160 can be an infusion pump, a syringe, a compressor, a pressurized container, and/or a gravity-based infusion mechanism.

Figure 3:
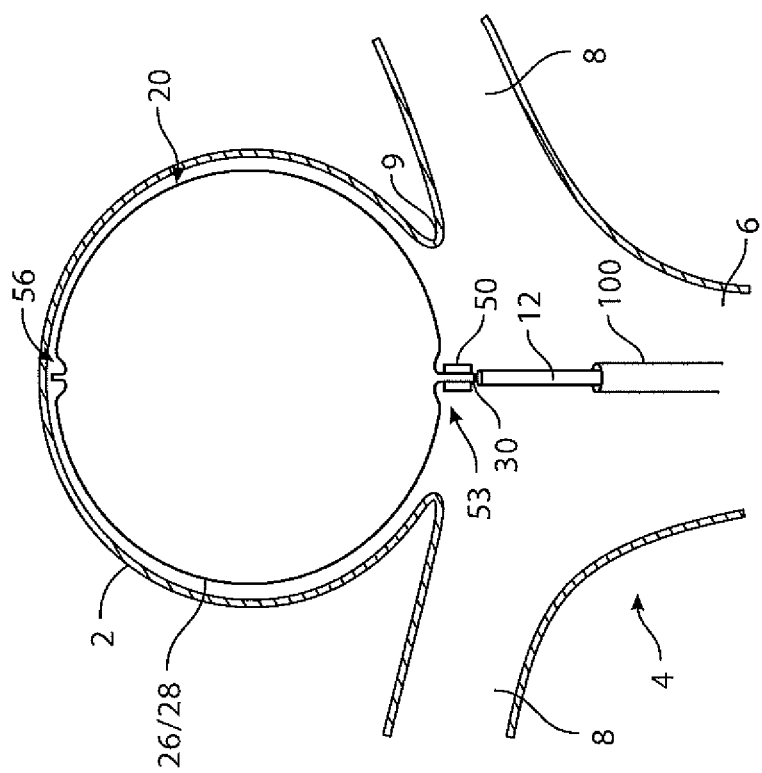
FIG. 3 shows a side-sectional view of the braid ball implant of FIG. 2 deployed within a bifurcation aneurysm, in accordance with one or more embodiments of the present disclosure.
Figure 2:
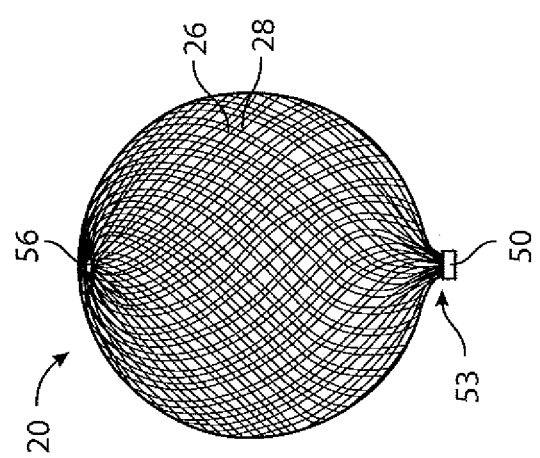
FIG. 2 shows a perspective side view of a braid ball implant, in accordance with one or more embodiments of the present disclosure.

According to some embodiments, for example as shown in FIGS. 2 and 3, an implant 20 delivered by the delivery system 10 can be a braid ball implant. The implant 20 can be formed from tubular braid stock including a resilient material, such as nitinol, that defines an open volume in an uncompressed/unconstrained state. The size of the implant can be selected to fill an aneurysm 2 when expanded therein. The implant 20 can include a hub 50 and layers 26, 28. The hub can be located at a proximal end 53 of the implant. The hub 50 can be fixedly attached to the remainder of the implant 20. For example, the hub 50 can grasp braided filaments of the layers 26, 28 of the implant 20. The implant 20 can include the layers 26, 28 at least where impacted by flow at the neck 9 of the aneurysm 2.

While the implant 20 illustrated herein is a braided ball, the implant 20 can be any well-known treatment device including, but not limited to, vasoocclusive coils, stents, filters, or flow diverters.

According to some embodiments, the implant 20 can be set within an aneurysm 2 at a vascular bifurcation 4, formed by trunk vessel 6 and branch vessels 8, for example as illustrated in FIG. 3. The implant 20 can be delivered by access through the trunk vessel 6 (e.g., the basilar artery), preferably through a commercially available microcatheter with a delivery system as detailed below. To deliver the implant 20, the pusher assembly 12 is positioned such that the implant 20 can be delivered at least partially into the aneurysm 2. When the implant is positioned in the aneurysm, the implant 20 is separated from the remainder of the pusher assembly 12 by electrolytic corrosion at the detachment zone 30, and the remainder of the pusher assembly 12 is withdrawn into the delivery catheter 100.

Figure 4:
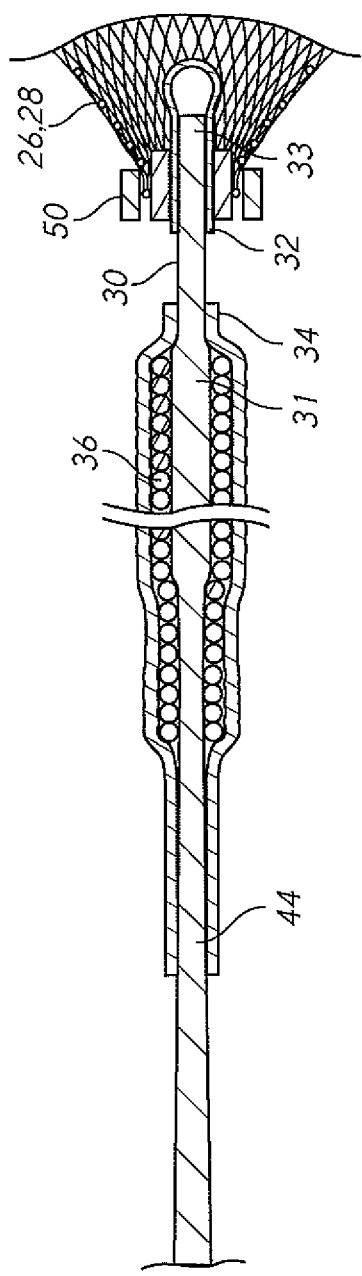
FIG. 4 shows a sectional view of a distal end of the delivery system of FIG. 1, in accordance with one or more embodiments of the present disclosure.

FIG. 4 illustrates a sectional view of a pusher assembly 12 according to one or more embodiments of the subject technology. According to some embodiments, for example as shown in FIG. 4, a pusher assembly 12 includes a delivery wire 44 having a proximal region 31, a distal region 33, and a detachment zone 30 between the proximal region 31 and the distal region 33. The delivery wire 44 can form a single, monolith component across the proximal region 31, the distal region 33, and the detachment zone 30, or the delivery wire 44 can be formed of separate segments joined together.

According to some embodiments, portions of the delivery wire 44 can be coated with a nonconductive material so that only a limited portion of surface area of the delivery wire is exposed to, and in electrical communication with, the electrolyte for corrosion when a voltage potential is applied. Limiting the size of the exposed portion of the surface area of the delivery wire can concentrate electrolytic activity to expedite corrosion through and severance of the delivery wire. A proximal insulating layer 34 can be provided over at least a portion of an outer surface of the proximal region 31. For example, the proximal insulating layer 34 can circumferentially surround an outer surface of the proximal region 31 extending proximally from a proximal end of the detachment zone 30 to a location at or near a proximal end of the delivery wire 44. According to some embodiments, a distal insulating layer 32 can be provided over at least a portion of an outer surface of the distal region 33 extending distally from a distal end of the detachment zone 30 to a distal terminal end of the delivery wire 44. For example, the distal insulating layer 32 can circumferentially surround and cover the entire outer surface of the distal region 33.

According to some embodiments, proximal and distal insulating layers 34, 32 leave exposed the portion of the delivery wire 44 forming the detachment zone 30 between the proximal region 31 and the distal region 33. When in contact with a body fluid, such as blood, the fluid serves as an electrolyte allowing current to be focused on the non-coated detachment zone 30. The proximal and distal insulating layers 34, 32 prevent exposure of the proximal region 31 and the distal region 33 to the fluid. Accordingly, electrical energy conducted along the delivery wire 44 is concentrated at the detachment zone 30, thereby reducing the time required to erode away the detachment zone 30. The proximal and distal insulating layers 34, 32 can be overmolded, co-extruded, sprayed on, or dip-coated with respect to the proximal region 31 and/or the distal region 33.

The distal insulating layer 32 also prevents electrical connection between the delivery wire 44 and the implant. As shown in FIG. 4, the distal insulating layer 32 electrically isolates the implant 20 from an electrical current conducted along a length of the delivery wire, from the proximal region 31 to the distal region 33. A proximal end of the distal insulating layer 32 may be positioned at or proximal to the hub 50, and a distal end of the distal insulating layer 32 may be positioned at or distal to the hub 50. Likewise, a proximal end of the distal region 33 may be positioned proximal to the hub 50, and a distal end of the distal region 33 may be positioned within or distal to the hub 50. The distal insulating layer 32 insulates the distal region 33 from the hub 50 to prevent the electrical current from being conducted to the implant 20.

The proximal and distal insulating layers 34, 32 can comprise an electrically nonconductive or insulative polymer, such as polyimide, polypropylene, polyolefins, or combinations thereof. In some embodiments, the proximal and distal insulating layers 34, 32 can be applied as a single coating with a portion thereof subsequently removed to expose the detachment zone 30. Laser ablation can be employed to selectively remove the coating to a controlled length, minimizing the time required to erode through the component. Lengths as small as 0.0005" and as large as 0.1" or longer can be removed. According to some embodiments, lengths of detachment zone 30 can be greater than 0.005" and/or less than 0.010" to provide sufficient exposure to achieve detachment times of less than 30 seconds.

The delivery wire 44 (including some or all of the proximal region 31, the distal region 33, or the detachment zone 30) can comprise one or more of the following materials: ceramic materials, plastics, base metals or alloys thereof, or combinations thereof. Some of the most suitable material combinations for forming the electrolytically corrodible points can include one or more of the following: stainless steels, preferably of the type AISI 301, 304, 316, or subgroups thereof; Ti or TiNi alloys; Co-based alloys; noble metals; or noble metal alloys, such as Pt, Pt metals, Pt alloys, Au alloys, or Sn alloys. In some embodiments, the electrolytically corrodible detachment zone can be pre-corroded by etching or other methods. According to some embodiments, a marker coil 36 is wound helically about an outer surface of the proximal insulating layer 34. The marker coil 36 can be of a radiopaque material, such as platinum, gold, palladium, iridium, and alloys thereof. The proximal insulating layer 34 can be provided about an outer surface of the marker coil 36. For example, as shown in FIG. 4, the proximal insulating layer 34 can extend over an entire length of the marker coil 36 and distally beyond the marker coil 36, such that every portion of the marker coil 36 is covered by the proximal insulating layer 34.

According to some embodiments, for example as shown in FIG. 4, the delivery wire 44 can be continuous through the proximal region 31. Accordingly, an electric potential applied to the proximal end of the delivery wire 44 can induce an electrical current conducted through the delivery wire 44 along the proximal region 31 to the detachment zone 30. Furthermore, an axial force applied to the delivery wire 44 can result in an axial movement of the detachment zone 30 and the implant 20.

Figure 5:
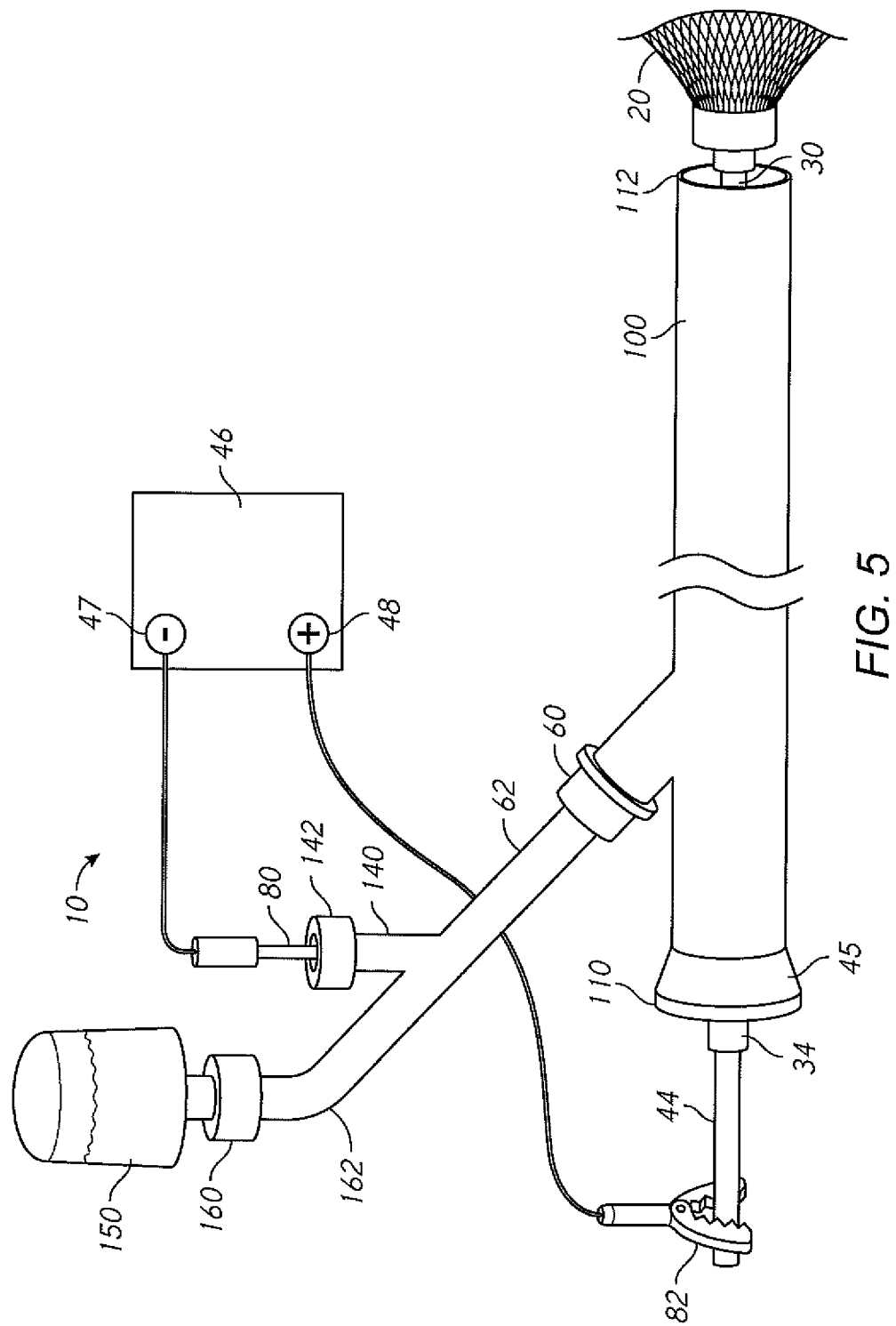
FIG. 5 shows a side view of the delivery system of FIG. 1, in accordance with one or more embodiments of the present disclosure.
Figure 6:
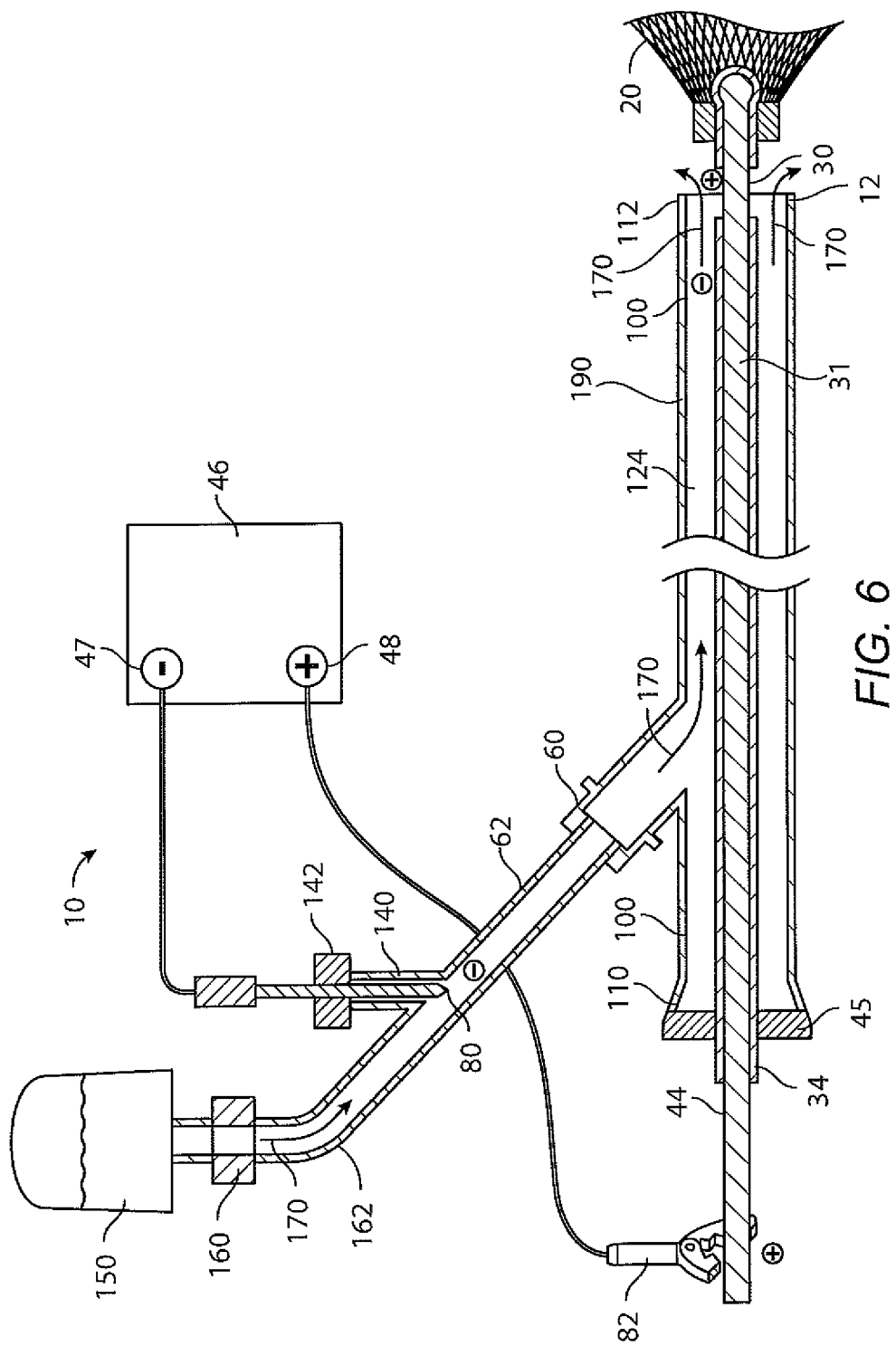
FIG. 6 shows a sectional view of the delivery system of FIGS. 1 and 5, in accordance with one or more embodiments of the present disclosure.

FIGS. 5 and 6 illustrate various views of a delivery system 10 according to some embodiments of the subject technology. FIG. 5 depicts a side view of a delivery system 10 and FIG. 6 depicts a sectional view of the delivery system 10 as shown in FIG. 5. The delivery system 10 illustrated in FIGS. 5 and 6 is similar in some respects to the delivery system 10 of FIG. 1 and can be understood with reference thereto, where like numerals indicate like elements or components not described again in detail. FIGS. 5 and 6 illustrate electrical connection of a power supply 46 to a delivery wire 44 and a fluid and/or fluid flow 170 in a vicinity of the detachment zone 30 of the delivery wire 44. An electrical pathway can pass from a first terminal 48 of the power supply to the delivery wire 44 and into a fluid/fluid flow 170 at the detachment zone 30, and then return to a second terminal 47 of the power supply 46 through the fluid/fluid flow.

According to some embodiments, for example as shown in FIGS. 5 and 6, the delivery catheter 100 can be formed as a generally tubular member with a body extending from a proximal end 110 and terminating in a distal end 112. An inner lumen 124 extends from a proximal port 45 of the delivery catheter 100. The delivery catheter 100 can generally track over a conventional guidewire and may be any commercially available microcatheter appropriate for such applications. Inner lumen 124 of the delivery catheter generally has an inner diameter between about 0.01 inch and about 0.098 inch (0.25-2.49 mm). Other designs and dimensions are contemplated. Commercially available microcatheters which may be suitable for use as delivery catheters include the REBAR™ Reinforced Micro Catheter, which is available from Medtronic, Inc. and the MARKSMAN™ Catheter, which is available from Medtronic, Inc.

According to some embodiments, the proximal port 45 of the delivery catheter 100 may be provided with an adapter (not shown) having a hemostatic valve. The proximal port 45 may comprise a valve or other sealable mechanism for receiving at least a portion of the pusher assembly 12 while preventing passage of the fluid flow 170 proximally past the proximal port 45 in the presence or absence of the delivery wire 44. For example, the proximal port 45 can include a split septum, slit valve, duckbill valve, dome valve, donut valve, multi-cuspid valve, or combinations thereof. The proximal port 45 can include a hydrophobic coating.

The delivery catheter 100 is generally constructed to bridge between a femoral artery access site and a cervical region of the carotid or vertebral artery and may be chosen according to several standard designs that are generally available. Accordingly, the delivery catheter 100 may be at least 85 cm long, and more particularly may be between about 95 cm and about 175 cm long. For example, a distance between (a) the proximal port 45 and/or the infusion port 60 (FIG. 5) and (b) the distal end 112 can be at least 85 cm, and more particularly may be between about 95 cm and about 175 cm long.

According to some embodiments, at least a portion of the delivery wire 44 extends through the proximal port 45 at the proximal end 110 of the delivery catheter 100. A delivery electrode 82 is configured to be coupled to the delivery wire 44. A variety of coupling mechanisms may be employed to selectively secure the delivery electrode 82 to the delivery wire 44 such that an electrical connection is established. For example, the delivery electrode 82 can include a clamp, pin, ring, clasp, or combinations thereof to engage a complementary structure of the delivery wire 44. The delivery electrode 82 is further configured to be coupled to the first terminal 48 (e.g., cathode or anode) of the power supply 46. An electrical potential generated at the first terminal 48 can induce an electrical current through the delivery electrode 82 and the delivery wire 44 to the detachment zone 30. Flow of electrical current between the delivery wire and the immediately surrounding environment (e.g., the fluid and/or fluid flow 170) can be focused at the detachment zone 30 by insulating a length of the delivery wire 44 with the proximal insulating layer 34 at least from the proximal port 45 to the detachment zone 30. At least a portion of the proximal insulating layer 34 may extend to the proximal port 45 and/or proximally thereof to insulate the delivery wire 44 from the fluid flow 170 within the lumen 124 of the delivery catheter 100.

According to some embodiments, an infusion connector 62 can provide a connection to the infusion port 60 for infusion of fluid and electrical connections. The infusion connector 62 can connect to an interface with the infusion port 60 on a first end. The infusion connector 62 can further provide an electrode connector 140 and a fluid connector 162. The infusion connector 62 can define a lumen that divides and connects to both an electrode port 142 of the electrode connector 140 and the pump 160 and fluid source 150 of the fluid connector 162.

The entirety or a portion of the infusion connector 62 and components thereof can be located outside a body of the patient. For example, the fluid connector 162, the electrode connector 140, the electrode port 142, the pump 160, and/or the fluid source 150 can be located outside a body of the patient during use. Further, components interfacing with the infusion connector 62 and components thereof can be located outside a body of the patient.

The infusion connector 62 can take the form of a Y-connector. Additional connectors can be provided in addition to the electrode connector 140 and the fluid connector 162. The interior lumens of the infusion connector 62 provide fluid communication and electrical connection through the fluid and between the infusion port 60, the electrode port 142, and the fluid source 150. Through the fluid 170 and the infusion port 60, the components of the infusion connector 62 can be placed in fluid communication and electrical connection with the lumen 124 of the delivery catheter 100, as well as components residing in and near the lumen 124, including the detachment zone 30.

According to some embodiments, the electrode connector 140 is configured to receive an infusion electrode 80. In some embodiments, at least a portion of the infusion electrode 80 extends distally through the electrode port 142 and at least a portion of the lumen of the electrode connector 140. In some embodiments, such as that shown in FIGS. 5 and 6, the infusion electrode 80 extends through the electrode connector 140 and into the lumen of the infusion connector 62. In some embodiments, the infusion electrode 80 may extend through the infusion connector 62 and through the infusion port 60. In some embodiments the infusion electrode 80 may extend into the lumen 124 of the delivery catheter 100 such that the distal tip of the infusion electrode 80 terminates within the lumen 124. In some embodiments, the infusion electrode 80 extends distally along the length of the delivery catheter 100 within the lumen 124 such that the distal tip of the infusion electrode 80 terminates within 2 inches of the detachment zone 30, and in some embodiments within 1 inch of the detachment zone 30. In any of the foregoing embodiments, at least a portion of the infusion electrode 80 between the second terminal 47 and a region adjacent the detachment zone 30 may be electrically insulated so long as the portion of the infusion electrode 80 within 2 inches of the detachment zone 30 is exposed (e.g., in electrical communication with the fluid pathway).

The infusion electrode 80 is configured to pass through the electrode port 142 to contact and/or be in electrical connection with the fluid 170 within the infusion connector 62 and/or the delivery catheter 100. For example, the infusion electrode 80 can comprise a needle or other elongate member. The electrode port 142 may comprise a valve or other sealable mechanism for receiving at least a portion of the infusion electrode 80 while preventing passage of the fluid flow 170 proximally past the electrode port 142 in the presence or absence of the infusion electrode 80. For example, the electrode port 142 can include a split septum, slit valve, duckbill valve, dome valve, donut valve, multicuspid valve, or combinations thereof. The electrode port 142 can include a hydrophobic coating. Alternatively or in combination, the infusion electrode 80 can be placed in electrical connection with the fluid 170 without directly contacting the fluid 170. For example, the infusion electrode 80 can include a clamp, pin, ring, clasp, or combinations thereof to engage the electrode port 142, thereby placing the infusion electrode 80 in electrical connection with the fluid 170.

The infusion electrode 80 is further configured to be coupled to the second terminal 47 (e.g., cathode or anode) of the power supply 46. An electrical potential generated at the second terminal 47 can induce an electrical current through the infusion electrode 80 and the fluid 170 (e.g., along the lumen 124) to the vicinity of the detachment zone 30. The infusion electrode 80 can be a "painted" electrode on a surface of a nonconductive material. The infusion electrode 80 can include platinum, platinum alloys (e.g., 92% platinum and 8% tungsten, 90% platinum and 10% iridium), gold, cobalt-chrome, stainless steel (e.g., 304 or 316), and combinations thereof.

According to some embodiments, an electrical pathway can pass through one or more of the first terminal 48 of the power supply 46, the delivery electrode 82, the proximal region 31 of the delivery wire 44, the detachment zone 30, the fluid 170 in the lumen 124 of the delivery catheter 100, the fluid 170 in the infusion port 60, the fluid 170 in the fluid connector 162, the fluid 170 in the electrode connector 140, the infusion electrode 80, the electrode port 142, and the second terminal 47 of the power supply 46. Other pathways completing a circuit can include other components or regions.

According to some embodiments, an infusion fluid 170 can be provided from the fluid source 150 to the infusion port 60, shown in FIGS. 5 and 6, to provide fluid communication to the distal end 112 of the delivery catheter 100. The fluid can be biocompatible and generally conductive.

Infusion may be accomplished by the pump 160 or other flow-inducing device. The infusion port 60 can be provided in fluid communication with and electrical connection with a distal end 112 of the delivery catheter 100.

In some embodiments, the infusion electrode 80 may be integrated with the body of the delivery catheter 100 such that the infusion electrode 80 extends distally within the sidewall 190 of the delivery catheter 100 rather than within the lumen 124 of the delivery catheter 100. In such embodiments, for example, the infusion electrode 80 may extend distally from the proximal end 110 of the delivery catheter 100 to a transmission portion adjacent the detachment zone 30. At least a region of the transmission portion may be exposed to the lumen 124 such that, when fluid 170 flows through the lumen 124 and the power supply 46 is providing a voltage across the first and second terminals 48, 47, an electrical current passes through the first terminal 48 of the power supply 46, the delivery electrode 82, the proximal region 31 of the delivery wire 44, the detachment zone 30, the fluid 170 in the lumen 124 of the delivery catheter 100, the transmission portion, the infusion electrode 80, and the second terminal 47 of the power supply 46.

In some embodiments, the exposed region of the transmission portion is located along the length of the delivery catheter 100 within 2 inches of the detachment zone 30. In some embodiments, the exposed region of the transmission portion is located along the length of the delivery catheter 100 within 1-2 inches of the detachment zone 30. In some embodiments, the exposed region of the transmission portion is located along the length of the delivery catheter 100 within 1 inch of the detachment zone 30.

In some embodiments, the transmission portion and the infusion electrode 80 are a single, continuous component or material (e.g., integral with one another), and the transmission portion may be a portion of the infusion electrode 80 that is exposed to the lumen 124. For example, in some embodiments the infusion electrode 80 may be an elongated, conductive member (e.g., a wire) that is insulated within the sidewall 190 of the delivery catheter 100, and the transmission portion is a portion of the conductive member that is exposed to the lumen 124 through the sidewall 190 within 2 inches of the detachment zone 30. In certain embodiments, the sidewall 190 of the delivery catheter 100 includes a coil and/or braid along its length that include one or more conductive materials. In such embodiments, a proximal end portion of the coil and/or braid can be electrically coupled to the second terminal 47 of the power source (directly or indirectly via one or more connectors) and a distal end portion of the braid and/or coil may be exposed through the sidewall 190 to the lumen 124 within 2 inches of the detachment zone. In some embodiments, a distal end portion of the braid and/or coil may be exposed through the sidewall 190 to the lumen 124 within 1-2 inches of the detachment zone, and in some embodiments within 1 inch of the detachment zone. As such, the transmission portion may be the exposed length of the coil and/or braid, and the infusion electrode 80 may be the length of the coil and/or braid between the second terminal 47 and the exposed portion.

In some embodiments, the transmission portion and the infusion electrode 80 are separate components that are electrically coupled to one another. For example, in some embodiments the infusion electrode 80 may be a first conductive element (e.g., a wire, a braid, a coil, etc.) that is insulated within the sidewall 190 of the delivery catheter 100, and the transmission portion is a second conductive element (e.g., all or part of a marker band, a braid, a coil, etc.) having at least a region exposed to the lumen 124 through the sidewall 190 within 2 inches of the detachment zone 30. In some embodiments, the second conductive element has at least a region exposed to the lumen 124 through the sidewall 190 within 1-2 inches of the detachment zone 30, and in some embodiments within 1 inch of the detachment zone. In any of the foregoing embodiments, a distal end portion of the infusion electrode 80 may be electrically coupled to a proximal end portion of the transmission portion.

Figure 7:
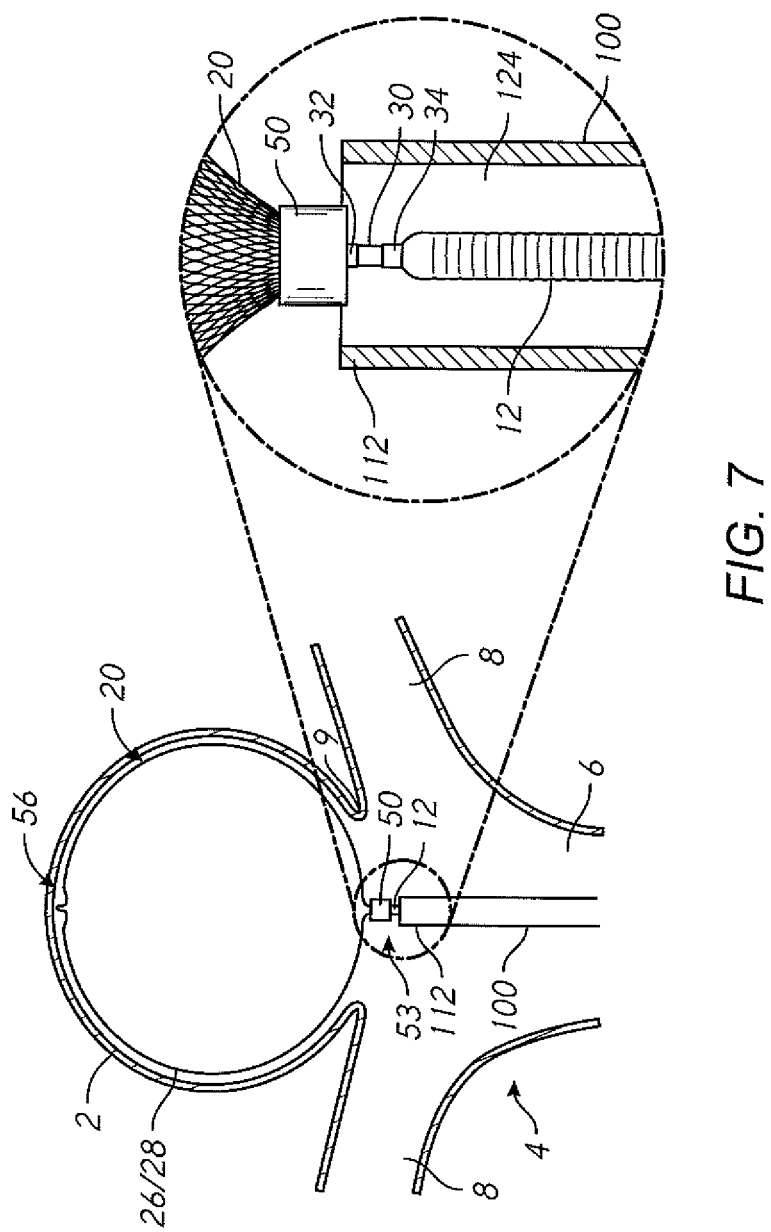
FIG. 7 shows a partial sectional view of an implant detachment zone at a stage of implant deployment within a bifurcation aneurysm, in accordance with one or more embodiments of the present disclosure.
Figure 8:
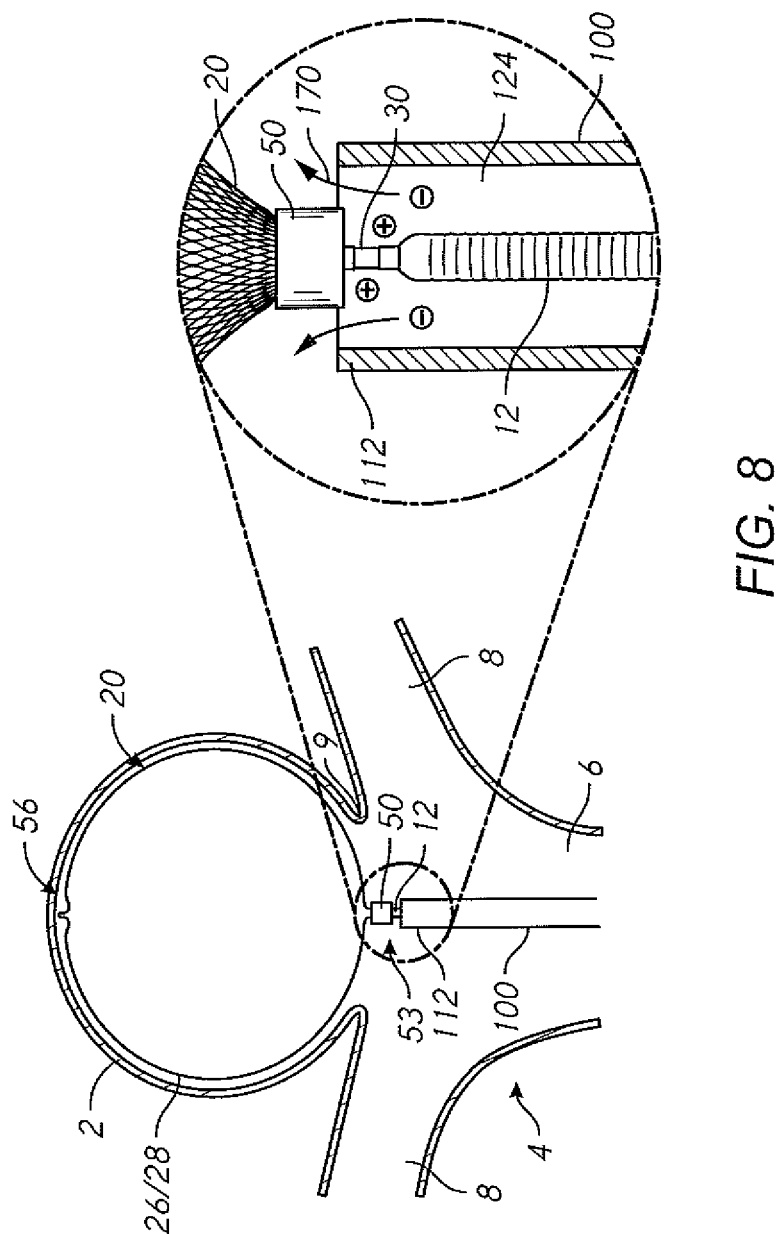
FIG. 8 shows a partial sectional view of an implant detachment zone at a stage of implant deployment within a bifurcation aneurysm, in accordance with one or more embodiments of the present disclosure.
Figure 9:
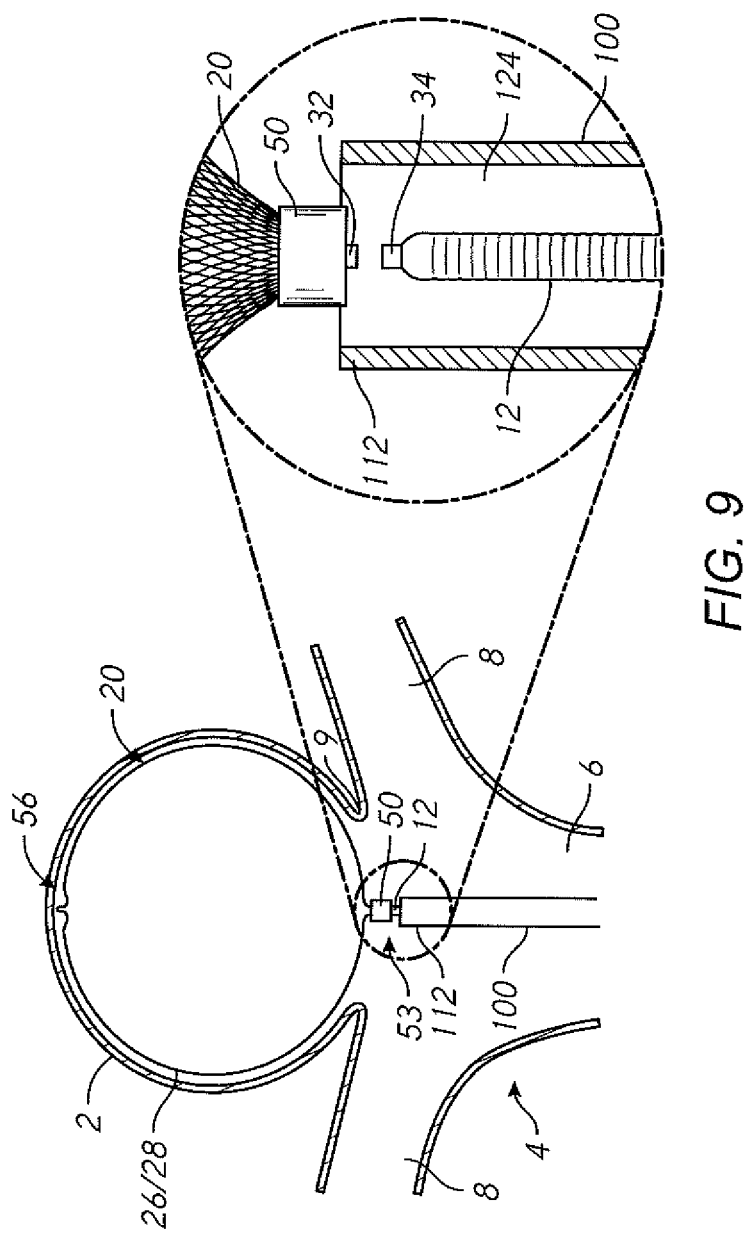
FIG. 9 shows a partial sectional view of an implant detachment zone at a stage of implant deployment within a bifurcation aneurysm, in accordance with one or more embodiments of the present disclosure.

FIGS. 7-9 illustrate various stages of an exemplifying method according to one or more embodiments of the subject technology. FIG. 7 illustrates an implant 20 inserted within the aneurysm 2. FIG. 8 illustrates a stage of detachment in progress FIG. 9 illustrates a stage following detachment of the implant 20 from the pusher assembly 12.

According to some embodiments, for example as shown in FIG. 7, the delivery catheter 100 is advanced to place its distal end 112 in the vicinity of a target site (e.g., an aneurysm 2). In addition to the components and steps shown herein, other components and stages may also be employed. For example, the delivery catheter 100 may be guided to the target site by a guide wire and/or a guide catheter, according to known techniques.

According to some embodiments, the implant 20 can be advanced over a guidewire (not shown) through the lumen 124 to the target site. For example, as shown in FIG. 7, the implant 20 can be placed within the aneurysm and deployed. As further shown in FIG. 7, the implant 20 is advanced from the delivery catheter 100 to the target site. Alternatively or in combination, the implant 20 may be placed at the target site, and the delivery catheter 100 may be subsequently advanced or retracted relative to the pusher assembly 12 while the pusher assembly 12 holds the implant 20 steady. The delivery catheter 100 may be positioned such that the detachment zone is entirely exposed, partially exposed, or not exposed by the delivery catheter 100. For example, the detachment zone 30 may be distal to, overlapping with, or proximal to the distal end 112 of the delivery catheter 100. In some embodiments, the detachment zone 30 can be longitudinally aligned with the distal end of the delivery catheter 100. Positioning of the delivery catheter 100 relative to the pusher assembly 12 (e.g., relative to the detachment zone 30) and/or implant 20 may be facilitated by components providing visualization. For example, a radiopaque marker of the delivery catheter 100 can be longitudinally aligned with a radiopaque marker of the pusher assembly 12 and/or the implant 20 to provide confirmation that the implant 20 is positioned outside of the delivery catheter 100.

According to some embodiments, for example as shown in FIG. 8, electrolytic detachment of the implant 20 from the pusher assembly 12 can be achieved. One or both of the detachment zone 30 and the infusion electrode 80 can be energized to apply electrical energy. For example, the detachment zone 30 and the infusion electrode 80 can be energized with electrical energy of opposite polarity to create a voltage potential and pass electrical current through the fluid 170 between the detachment zone 30 and the infusion electrode 80. While the electrical current can pass predominantly through the fluid 170, current induced by the voltage potential may also pass along other pathways. Fluids other than the fluid 170 from the fluid source 150 can contribute to an electrical pathway. For example, blood from the body of the patient may mix with the fluid 170 and form a portion of the pathway.

During detachment, a current source (e.g., the power supply 46) connected to the detachment zone 30 is activated and/or a current source connected to the infusion electrode 80 is activated. While one of the detachment zone 30 and the infusion electrode 80 are energized, the other can be energized with an opposite polarity or grounded. According to some embodiments, during operation, the detachment zone 30 and the infusion electrode 80 can each be multifunctional. For example, each can serve as either an active electrode or a ground electrode at different points in time as the treatment proceeds. By further example, each can serve as either a cathode or an anode at different points in time as the treatment proceeds. If desired, during the period of time that a voltage potential is formed, the polarity can be switched once or repeatedly, to create currents traveling in either direction across the gap between the detachment zone 30 and the infusion electrode 80.

According to some embodiments, for example as shown in FIG. 8, fluid flow 170 can be provided during electrolytic detachment of the implant 20 from the pusher assembly 12. For example, an infusion of fluid from the fluid source 150 by the pump 160 can be provided via the delivery catheter 100 past the detachment zone 30. The fluid flow 170 can be directed distally from the lumen 124 to a region distal to the distal end 112 of the delivery catheter 100. Alternatively the fluid flow 170 can be directed proximally into the lumen 124 from a region distal to the distal end 112 of the delivery catheter 100.

According to some embodiments, the fluid flow 170 may evacuate any bubbles that form near the detachment zone 30. The formation of bubbles can also change the dielectric characteristics of the vicinity of the detachment zone 30. For example, bubbles can serve as a dielectric material and electrically insulate the detachment zone 30 from the infusion electrode 80. Such a condition can create a dielectric region with an undesirably high breakdown voltage. The fluid flow 170 can refresh the fluid composition within the gap to maintain a clear conduction path.

According to some embodiments, the fluid flow 170 may evacuate debris from the vicinity of the detachment zone 30. For example, as portions of the detachment zone 30 are released into the vicinity of the detachment zone 30, the debris can form or facilitate a short circuit from the detachment zone 30 to other structures, thereby creating a conductive bridge and reducing the rate of electrolytic detachment of the detachment zone 30. The fluid flow 170 can remove the debris to maintain a clear pathway for electrical current between the detachment zone 30 and the infusion electrode 80.

According to some embodiments, the fluid flow 170 can be provided during part or all of an electrolytic detachment operation. For example, the fluid flow 170 may commence before, during, or after initial application of a voltage potential between the detachment zone 30 and the delivery catheter 100. By further example, the fluid flow 170 may cease before, during, or after termination of the voltage potential.

According to some embodiments, the fluid flow 170 can be provided intermittently based on conditions existing during the electrolytic detachment process. For example, the fluid flow 170 can be provided when and/or only when the power supply 46 outputs a voltage and/or current above and/or below a threshold. For example, if a controller of the power supply 46 detects an increase (e.g., short circuit) or decrease (e.g. open circuit) of current flow between the detachment zone 30 and the infusion electrode 80, the fluid flow 170 can be controllably provided until the current flow normalizes to a desired value or range of values, representative of efficient electrolytic corrosion. The flow of fluid can be continuous throughout a stage or an entirety of a process. The flow can have an increased rate during portions of a process to remove debris and reduce thrombus formation.

According to some embodiments, for example as shown in FIG. 9, full corrosion of the detachment zone 30 results in the implant 20 being entirely separated from the pusher assembly 12. Upon detachment, the fluid flow 170 can cease, and the pusher assembly 12 and the delivery catheter 100 can be retracted away from the target site and out of the patient, leaving the implant 20 at the target site.

Embodiments disclosed herein can be used in veterinary or human medicine and more particularly, for the endovascular treatment of intracranial aneurysms and acquired or innate arteriovenous blood vessel deformities and/or fistulas and/or for the embolization of tumors.

The apparatus and methods discussed herein are not limited to the deployment and use of an occluding device within any particular vessels, but can include any number of different types of vessels. For example, in some embodiments, vessels can include arteries or veins. In some embodiments, the vessels can be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some embodiments, the stent delivery systems disclosed herein can be deployed within superthoracic vessels. The suprathoracic vessels can include at least one of intracranial vessels, cerebral arteries, and/or any branches thereof. In some embodiments, the stent delivery systems disclosed herein can be deployed within intrathoracic vessels. The intrathoracic vessels can include the aorta or branches thereof. In some embodiments, the stent delivery systems disclosed herein can be deployed within subthoracic vessels. In some embodiments, the stent delivery systems disclosed herein can be deployed within lateral thoracic vessels.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa. It is understood that the specific order or hierarchy of steps in the processes disclosed is an illustration of exemplifying approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A delivery system comprising:
   a catheter having a proximal end region, a distal end region, and a lumen extending from the proximal end region to the distal end region along a length that facilitates access from an entry region outside of a patient to a target location within the patient;
   a delivery wire having a proximal end portion, a distal end portion, and an electrolytically corrodible detachment zone between the proximal and distal end portions, the electrolytically corrodible detachment zone having a first diameter and at least a portion of the distal end portion having a second diameter substantially the same or larger than the first diameter, the delivery wire extending through at least a portion of the lumen;
   a distal layer disposed over the distal end portion of the delivery wire and configured to electrically insulate the outer surface of the distal end portion;
   an implant attached to the delivery wire distal to the electrolytically corrodible detachment zone;
   a fluid source configured to be in fluid communication with the distal end region via the proximal end region and the lumen;
   a delivery electrode configured to contact the delivery wire and electrically connect to the electrolytically corrodible detachment zone via the delivery wire; and
   an infusion electrode integrated with an outer body of the catheter and extending in a longitudinal direction, the infusion electrode being configured to contact fluid within the lumen and extend distally toward the electrolytically corrodible detachment zone, the infusion electrode configured to electrically connect to the electrolytically corrodible detachment zone via the fluid within the lumen, wherein a portion of the infusion electrode extending in the longitudinal direction and at a region adjacent the electrolytically corrodible detachment zone is electrically insulated.

2. The delivery system of claim 1, further comprising a pump configured to provide a flow of the fluid within the lumen to the detachment zone.

3. The delivery system of claim 1, further comprising a power supply connected to the delivery electrode and the infusion electrode.

4. The delivery system of claim 3, wherein the power supply is configured to provide a voltage potential between the delivery electrode and the infusion electrode.

5. The delivery system of claim 1, wherein the delivery electrode contacts the delivery wire at the entry region outside the patient.

6. The delivery system of claim 1, wherein the detachment zone is of a material that is more susceptible to electrolytic corrosion than a material of the delivery wire or a material of the implant.

7. The delivery system of claim 1, wherein the fluid comprises saline.

8. The delivery system of claim 1, wherein the infusion electrode extends within a sidewall of the catheter from the proximal end region of the catheter to the distal end region of the catheter.

9. The delivery system of claim 8, wherein a portion of the infusion electrode is exposed through the sidewall within 2 inches of the detachment zone.

10. The delivery system of claim 8, wherein a portion of the infusion electrode is exposed through the sidewall within 1 inch of the detachment zone.

11. The delivery system of claim 1, wherein the proximal end portion and the electrolytically corrodible detachment zone have substantially identical uniform diameters.

12. The delivery system of claim 1, wherein the delivery wire has a substantially uniform diameter along its length.

13. The delivery system of claim 1, further comprising a hub disposed at a proximal end of the implant, a distal end portion of the distal layer being distal to the hub.

14. A delivery system comprising:
   an elongate member having a distal end portion, and an electrolytically corrodible detachment zone proximal to the distal end portion, wherein the electrolytically corrodible detachment zone has a first diameter and at least a portion of the distal end portion has a second diameter at least as large as the first diameter;
   a catheter having a lumen extending along a length that facilitates access to a target location within a patient, the lumen configured to receive the elongate member and a fluid from a fluid source disposed outside the lumen;
   a distal insulating material disposed over the distal end portion of the elongate member, the distal insulating material configured to electrically insulate the outer surface of the distal end portion;

an implant attached to the elongate member distal to the electrolytically corrodible detachment zone;

a first electrode contacting the elongate member and electrically connected to the electrolytically corrodible detachment zone; and a second electrode integrated with an outer body of the catheter and extending in a longitudinal direction, the second electrode contacting the fluid within the lumen and forming at least part of a conductive path, the second electrode extending distally toward the electrolytically corrodible detachment zone and electrically connected to the electrolytically corrodible detachment zone via the fluid received by the lumen, wherein a portion of the conductive path extending in the longitudinal direction and at a region adjacent the electrolytically corrodible detachment zone is electrically insulated.

15. The delivery system of claim 14, wherein a tip of the second electrode is spaced apart from the electrolytically corrodible detachment zone by 2 inches or less.

16. The delivery system of claim 14, wherein the second electrode extends distally within a sidewall of the catheter.

\* \* \* \* \*